United States Patent [19]

Urban

[11] Patent Number: 5,326,884

[45] Date of Patent: Jul. 5, 1994

[54] PROCESS FOR OPTICALLY ACTIVE 3-(METHANE-SULFONYLOXY)THIOLANE AND ANALOGS

[75] Inventor: Frank J. Urban, Groton, Conn.

[73] Assignee: Pfizer Inc., New York, N.Y.

[21] Appl. No.: 515,924

[22] Filed: Apr. 27, 1990

Related U.S. Application Data

[62] Division of Ser. No. 382,602, Jul. 19, 1989, Pat. No. 4,954,647, which is a division of Ser. No. 183,102, Apr. 19, 1988, Pat. No. 4,874,877.

[51] Int. Cl.$^5$ ............................................. C07D 333/32
[52] U.S. Cl. ...................................................... 549/66
[58] Field of Search ............................ 558/46; 549/68

[56] References Cited

U.S. PATENT DOCUMENTS

| | | | |
|---|---|---|---|
| 4,619,924 | 10/1986 | Hamanaka | 514/195 |
| 4,739,047 | 4/1988 | Volkmann et al. | 540/310 |
| 4,864,046 | 9/1989 | Volkmann | 558/46 |
| 4,874,877 | 10/1989 | Urban | 549/66 |
| 4,954,647 | 9/1990 | Urban | 549/66 |

OTHER PUBLICATIONS

Feiser and Fieser, Advanced Organic Chemistry, pp. 313, 319 (1961).
Kleeman, et al., Angew. Chemie Int. Ed. Engl., 18, 797 (1979).
Steadman et al., J. Agric. Food Chem., 23, 1137–1143 (1975).

*Primary Examiner*—Alan Siegel
*Attorney, Agent, or Firm*—Peter C. Richardson; Gregg C. Benson; Mervin E. Brokke

[57] ABSTRACT

Intermediates and a stepwise process for the conversion of D-methionine or certain of its derivatives to optically active compounds of the formula

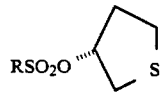

wherein R is $(C_1-C_3)$alkyl, phenyl or tolyl. The latter compounds are in turn useful as an intermediate in the preparation of penem antibiotic 5R,6S-6-(1R-hydroxyethyl)-2-(1R-oxo-3S-thiolanylthio)-2-penem-3-carboxylic acid and corresponding pharmaceutically acceptable salts and esters.

9 Claims, No Drawings

PROCESS FOR OPTICALLY ACTIVE 3-(METHANE-SULFONYLOXY)THIOLANE AND ANALOGS

This is a division of application Ser. No. 07/382,602, filed on Jul. 19, 1989, now U.S. Pat. No. 4,954,647, which is a division of application Ser. No. 07/183,102, filed Apr. 19, 1988, now U.S. Pat. No. 4,874,877.

BACKGROUND OF THE INVENTION

The present invention is directed to intermediates and a stepwise process for the conversion of D-methionine or certain of its derivatives to optically active 3-thiolanyl sulfonate esters of the formula

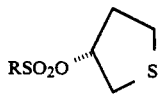
(I)

wherein R is $(C_1-C_3)$alkyl, phenyl or tolyl.

The compounds of formula (I) are particularly valuable intermediates in the preparation of certain penem antibiotics. Thus, antibacterial 5R,6S-6-(1R-hydroxyethyl)-2-(cis-1-oxo-3-thiolanylthio)-2-penem-3-carboxylic acid, which is a diastereomeric mixture of two compounds, was earlier disclosed as a valuable antibacterial substance by Hamanaka, U.S. Pat. No. 4,619,924; while Volkmann et al., in European patent application 222397, have disclosed an improved synthesis for that substance. More recently, the preferred diastereoisomer [5R,6S-6-(1R-hydroxyethyl)-2-(1R-oxo-3S-thiolanylthio)-2-penem-3-carboxylic acid] and a process therefor, have been identified by Yolkmann in as yet unpublished International Application No. PCT/US87/01114, designating inter alia the United States of America. Key to Volkmann's process is an optically active intermediate of the formula (I), prepared by the following sequence:

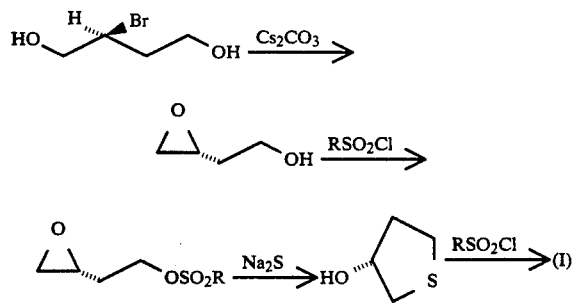

We have now found that the optically active compounds of the formula (I) are more conveniently and readily prepared from D-methionine, or derivatives thereof.

SUMMARY OF THE INVENTION

The present invention is particularly directed to a process for the preparation of an optically active compound of the formula

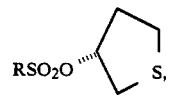
(I)

wherein R is $(C_1-C_3)$alkyl, phenyl or tolyl, which comprises the steps of:

(a) reacting an optically active diol of the formula

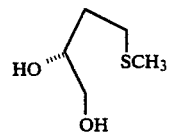
(II)

in a reaction-inert solvent with at least 2 molar equivalents of an activated form of a sulfonic acid of the formula $RSO_2OH$ in the presence of at least 2 equivalents of a tertiary amine (e.g., pyridine) to form an optically active disulfonate of the formula

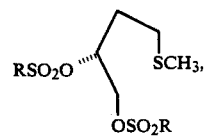
(III)

(b) with or without isolation, heating the disulfonate of the formula (III) neat or in the same or another reaction-inert solvent to form an optically active sulfonium salt of the formula

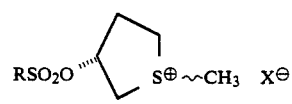
(IV)

wherein X is $RSO_3$ or halogen; and (c) with or without isolation, heating the sulfonium salt of the formula (IV) with up to three molar equivalents of an additional nucleophilic anion in the same or another reaction-inert solvent to form the compound of the formula (I).

The preferred activated form of the sulfonic acid is the sulfonyl chloride, $RSO_2Cl$. The preferred values of R are methyl and p-tolyl. It is preferred to carry out the process without isolation of the intermediate compounds of the formulas (III) and (IV), using substantially two equivalents of the sulfonyl chloride in an excess of pyridine, which serves not only as the tertiary amine, but also as solvent.

The present invention is also directed to the above process employing $RSO_2Cl$ which further comprises the preparation of the diol of the formula (II) via the following steps:

(d) diazotization of D-methionine with $NaNO_2$ in acetic acid to form an optically active acetoxy acid of the formula

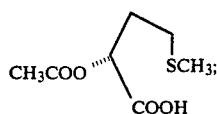

(e) concurrent solvolysis and esterification of the acetoxy acid of the formula (V) by reaction with excess methanol in the presence of a catalytic amount of a strong acid to form an optically active hydroxy ester of the formula

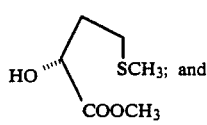

(f) hydride reduction of the hydroxy ester of the formula (VI) to form the diol of the formula (II).

The present invention is further directed to a process employing $RSO_2Cl$ in step (a) of above steps (a), (b) and (c) which further comprises oxidation of the product compound of the formula (I) to form an optically active sulfoxide of the formula

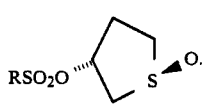

Finally, the present invention is directed to the above compounds of the formula (III) and (IV). Preferred such compounds have $X^\ominus$ as $RSO_3^\ominus$ and R as methyl or p-tolyl.

As employed above and elsewhere herein, the expression "reaction-inert solvent" refers to a solvent which does not interact with starting materials, reagents, intermediates or products in a manner which adversely affects the yield of the desired product.

DETAILED DESCRIPTION OF THE INVENTION

The present preparation of optically active thiolanyl sulfonate esters of the formula (I) from (S)-4-(methylthio)-1,2-butanediol (II) is readily carried out.

The preferred method is the so-called "one-pot" process in which the intermediates of the formula (III) and (IV) are not isolated. In this one-pot process it is preferred to combine the diol (II) with substantially 2 molar equivalents of the sulfonyl chloride of the formula $RSO_2Cl$ (where R is as defined above) in an excess (generally greater than 4 molar equivalents) of a tertiary amine (conveniently and preferably, pyridine), which also serves as solvent. The reaction is generally carried out initially at room temperature, but later heated (generally into the range of 50°-80° C.) to assure complete conversion to (I). The overall conversion is easily monitored by conventional thin layer chromatography (tlc) on silica gel, since the product (I), starting material (II) and intermediates (III) and (IV) have generally divergent Rf values using a variety of solvent systems as eluant. When $RSO_2Cl$ is employed as the sulfonylating agent in the one-pot process, it is unnecessary to add an additional nucleophilic anion, such as trifluoroacetic acid, to achieve the final step (III→I) of the transformation, since two molar equivalents of tertiary amine hydrochloride (i.e., nucleophilic $Cl^\ominus$) will be present from the sulfonation step.

Of course, by suitable modification of the conditions, either or both of the intermediates of the formulas (III) and (IV) can be isolated. Thus when isolation of the disulfonate ester of the formula (III) is desired, the reaction is preferably carried out in pyridine for a short reaction time, then diluted with water and the product extracted into an immiscible solvent such as ethyl acetate and isolated by evaporation of solvents at reduced pressure.

To convert the isolated disulfonate ester (III) to isolated thiolanium salt simply requires standing, at ambient temperature, preferably diluted with a reaction inert solvent such as $CHCl_3$ from which the desired salt will crystallize upon the addition of a non-solvent such as ethyl acetate. Of course, the extended reaction time required at room temperature can be substantially reduced by heating, e.g., to 40°-90° C. When the reaction is carried out in $CHCl_3$, the reflux temperature of the reaction mixture is particularly convenient.

To convert the isolated disulfonate ester (III) directly to 3-thiolanyl sulfonate of the formula (I), the isolated intermediate (III) is subjected to conditions analogous to those found in the one-pot process, viz., dissolution in excess tertiary amine (preferably pyridine) with, once conversion of (III) to (IV), in situ, is substantially complete, the addition of up to three equivalents of an acid (e.g. acetic acid, HCl, or, preferably trifluoroacetic acid) to facilitate the desired reaction by forming excess nucleophilic anion. It is particularly convenient to use excess pyridine as solvent and to introduce the excess anion in the form of 1-3 molar equivalents (preferably about 2 molar equivalents) of pyridinium trifluoroacetate.

If direct conversion of the diol (II) to isolated thiolanium salt (IV) is desired, it is most convenient to convert (II) to (III) as described above. In this case, less care need be taken in maintaining a low temperature in stripping away solvent, excess amine and amine salt, since premature cyclization to (IV) does not present a problem. The residual oil is then simply heated to 60°-95° C. to effect complete conversion to the desired thiolanium salt in which $X^\ominus$ is $RSO_3O^\ominus$. The latter is generally directly isolated by crystallization from a solvent such as ethyl acetate.

Isolated thiolanium salt (IV) is converted to the desired 3-thiolanium salt (I) by the method described above for the conversion of the disulfonate ester (III) directly to (I).

The optically active diol (II) required as starting material in the present invention is a known compound. It is preferably prepared by stepwise diazotization of commercially available D-methionine with $NaNO_2$ in acetic acid to form the optically active acetoxy acid of the formula (V), concurrent solvolysis and esterification of (V) to produce the hydroxy ester of the formula (VI), and hydride reduction, preferably with $NaBH_4$. Detailed methods therefor are disclosed in the Preparation section below. Alternative literature methods for the conversion of D-methionine to the diol (II), as well as alternative literature methods the preparation of (R)-4-(methylthio)-2-hydroxybutyric acid and (R)-4-(methylthio)-1,2-butanediol (II) from sources other than D-methionine, are cited in the Preparation section below.

The optically active 3-thiolanyl esters prepared according to the present invention are used in the preparation of 5R, 6S-6- (1R-hydroxyethyl) -2- (1R-oxo-3S-thi-olanylthio)-2-penem-3-carboxylate antibiotics of the formula

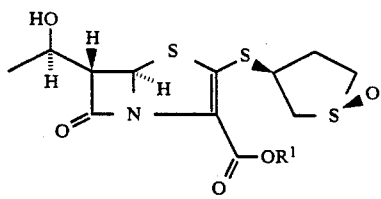

(VIII)

wherein $R^1$ is hydrogen or a radical hydrolyzed in vivo, or a pharmaceutically-acceptable salt thereof, according to methods which are fully disclosed in Examples below. As noted above, the compounds of the formula (VIII) are much preferred over the pair of diastereoisomers found in Hamanaka's 5R,6S-6-(1R-hydroxyethyl)-2-(cis-1-oxo-3-thiolanylthio)-2-penem-3-carboxylate substances. This is because these compounds, and their several immediate precursors, are single, homogeneous compounds, such that the quality of the final products is much better controlled relative to the previously reported diastereomeric mixture (an important factor in clinical use). In addition, the isomers (VIII) show clinical advantages over Hamanaka's diastereomeric mixture.

Concerning other starting materials required for the further processing to produce the penems (VIII), 3R,4R-4-acetoxy-3-[1R-1-(silyloxy)ethyl]-2-azetidinones are readily available according to the method of Leanza et al., cited above; and 2-chloroallyl oxalochloride is available from 2-chloroallyl alcohol and oxalyl chloride according to the methods detailed below.

The pure diastereomeric, antibacterial compounds of the formula (VII) are tested, formulated and used according to methods detailed in above cited Hamanaka, U.S. Pat. No. 4,619,924, hereby incorporated by reference. Within the human dosage ranges there disclosed, the more preferred dosage range for these compounds is about 10–80 mg/kg/day, both orally and parenterally. These figures are illustrative only, since in some circumstances the attending physician will find it more beneficial to employ dosages outside of these ranges. In vivo hydrolyzable esters, particularly the pivaloyloxymethyl and 1-(ethoxycarbonyloxy)ethyl esters, are preferred in oral use, while the sodium or potassium salts are particularly preferred for parenteral use.

The following examples are given by way of illustration and are not to be construed as limitations of this invention, many variations of which are possible within the scope and spirit thereof.

EXAMPLE 1

(R)-4-(Methylthio)-2-(p-toluenesulfonyloxy)butyl p-Toluenesulfonate (R)-4-(Methylthio)-1,2-butanediol (0.4 g, 2.9 mmol) was dissolved in 5 ml of pyridine and cooled to 0°–5° C. p-Toluenesulfonyl chloride (1.65 g, 9.0 mmol) was added and, after 5 minutes, the cooling bath removed, and the mixture stirred at room temperature for 2 hours, at which point it was diluted with 15 ml of H$_2$O and extracted with 20 ml of ethyl acetate. The organic extract was washed with saturated NaCl, dried (MgSO$_4$) and stripped to yield 0.5 g of present, crude title product as an oil, all of which was used in the next step without further refinement; tlc Rf 0.53 (3:1 hexane:ethyl acetate), 0.25 (5:1 hexane:ethyl acetate).

EXAMPLE 2

3R-Tosyloxy-1-methylthiolanium Tosylate

The entire product of the preceding Example (0.5 g) was dissolved in 15 ml CHCl$_3$ and, after standing at room temperature for 65 hours, refluxed for 4 hours. The mixture was cooled, stripped to an oil in vacuo, and the oil redissolved in the minimum necessary CHCl$_3$. Upon the addition of ethyl acetate, 0.18 g of present title product crystallized as a white solid; mp 148°–151° C.; $^1$H-NMR (CDCl$_3$, 250 MHz) delta (ppm) 7.75 (d, , 2H), 7.65 (d, 2H), 7.33 (d, 2H), 7.18 (d, 2H), 5.5 (bs, 1H), 4.18 (dd, 1H), 3.95 (d, 1H), 3.73 (dd, 1H), 3.48 (td, 1H), 3.24 (s, 3H), 2.7 (m, 1H), 2.4 (s+m, 4H), 2.35 ( s, 3H). The stereochemical orientation of the 1-methyl group has not been established, but it is probably R, i.e., trans to the p-toluenesulfonyloxy group.

EXAMPLE 3

(R)- 3-Thiolanyl-p-Toluenesulfonate (R)-4-(Methylthio)1,2-butanediol (1.0 g, 7.35 mmol) and p-toluenesulfonyl chloride (3.0 g, 15.8 mmol) were combined in 10 ml of pyridine at 0°–5° C., then stirred at room temperature, at which time tlc (3:1 hexane:ethyl acetate) indicated no diol (Rf 0.1), appreciable of the Example 1 ditosylate (Rf 0.53), some of the Example 2 thiolanium salt (Rf 0.03) and a trace of title product (Rf 0.72). The reaction mixture was then heated at 60° C. for 8 hours, at which time tlc (5:1 hexane:ethyl acetate) indicated an appreciable amount of the desired title product (Rf 0.45), only a trace of the ditosylate (Rf 0.22), some probable thiolanium salt (Rf 0.0), and other, generally less polar impurities. The cooled reaction mixture was diluted with an equal volume of water and two volumes of ethyl acetate. The organic layer was separated, washed with saturated NaCl, dried (MgSO$_4$), stripped and the residue chromatographed on silica gel using 10:1 hexane:ethyl acetate as eluant to yield 0.1 g less polar impurities (stench!) and 0.25 g of present, purified title product; tlc Rf 0.55 (4:1 hexane:ethyl acetate); [alpha]$_D$=15.87 (c=0.6, CH$_3$OH).

The same product is obtained by substituting a molar equivalent of the product of Example 2, for (R)-4-(methylthio)-1,2-butanediol in this process. Virtually identical conditions are obtained by introducing 2 molar equivalents of pyridine HCl into the reaction mixture. Alternatively the strong acid is introduced as pyridinium trifluoroacetate.

EXAMPLE 4

(R)-4-(Methylthio)-2-(methanesulfonyloxy)butyl Methanesulfonate (R)-4-(Methylthio)-1,2-butanediol (0.47 g, 3.4 mmol) was dissolved in 5 ml of pyridine and cooled to 0° C. Methanesulfonyl chloride (0.66 ml, 8.5 mmol) was added and the mixture stirred for 2 hours while warming to room temperature, by which time tlc (ethyl acetate) indicated complete conversion of starting material (Rf 0.4) to title product (Rf 0.85). The reaction mixture was diluted with 10 ml H$_2$O and extracted 2×15 ml of ethyl acetate. The organic layers were combined, dried (MgSO$_4$) and stripped to in vacuo to yield title product an an oil, all of which was used in the next step; tlc Rf 0.85 (ethyl acetate).

EXAMPLE 5

3R-(Methanesulfonyloxy)-1-methylthiolanium Methanesulfonate

Method A

The entire title product of the preceding Example was dissolved in 20 ml of CHCl$_3$ and heated to near reflux for 15 minutes, by which time some oily product had separated and the reaction mixture was milky. The CHCl$_3$ was stripped away and the tacky residue crystallized from hot isopropanol to yield 0.52 g of title product in two crops; mp 132°-134° C.; tlc Rf 0.03 (10:1 CHCl$_3$:ethyl acetate), 0.05 (ethyl acetate); $^1$H-NMR (CDCl$_3$), 250 MHz) delta (ppm) 5.68 (bs, 1H), 3.86 (m, 2H), 3.58 (m, 2H), 3.35 (s, 3H), 2.95 (s, 3H), 2.64 (m, 2H), 2.37 (s, 3H). The stereochemistry of the 1-methyl group has not been established, but is believed to be R, i.e., trans to the methanesulfonyloxy group.

Method B (R)-4-(Methylthio)-1,2-butanediol (1.4 g, 10 mmol) was dissolved in 10 ml of pyridine and cooled to 10° C. Methanesulfonyl chloride (1.9 ml, 25 mmol) was added and the mixture stirred at 0°-5° C. for 30 minutes and then for 2 hours at room temperature. The reaction mixture was diluted with 20 ml of H$_2$O and extracted with 30 ml of ethyl acetate. The organic layer was separated, dried (MgSO$_4$) and stripped to an oil, which was heated neat for 15 minutes, then cooled and triturated with ethyl acetate to yield 1.8 g of present title product identical in properties to that of Method A. The ethyl acetate triturate was stripped to an oil which tlc indicated was primarily the dimesylate product of Example 4. Upon heating this residue on a steam bath for 15 minutes, cooling and triturating with ethyl acetate, an additional 0.75 g of present title product was obtained.

EXAMPLE 6

(R)-3-Thiolanyl Methanesulfonate

Title product of the preceding Example (1.8 g, 6.5 mmol), pyridinium trifluoroacetate (2.5 g, 13 mmol) and 15 ml of pyridine were combined and warmed gently over a steam bath to obtain solution. The latter was stirred for 18 hours at room temperature, then stripped in vacuo and the residue triturated with 15 ml of ethyl acetate, and filtered from a tacky white solid precipitate. The filtrate was washed with 15 ml of H$_2$O, dried (MgSO$_4$), stripped to an oil, and the oil chromatographed on 8 g of silica gel using CHCl$_3$ as eluant to yield 0.18 g of purified title product; tlc Rf 0.65 (10:1 CHCl$_3$:ethyl acetate), 0.55 (1:1 hexane:ethyl acetate), 0.82 (5:1 ethyl acetate: methanol); [alpha]$_D$= +19.9 (c=0.17, CH$_3$OH); $^1$H-NMR (CDCl$_3$), 250 MHz) delta (ppm) 5.45 (m, $^1$H), 3.2-2.9 (s+m, 7H), 2.5 (m, 1H), 2.1 (m, 1H).

EXAMPLE 7

3R-(Methanesulfonyloxy) thiolane 1R-Oxide

A solution of title product of the preceding Example (0.17 g, 0.93 mmol) in 5 ml of acetone was cooled to 0°-5° C. and potassium peroxymonosulfate (Oxone®; 2KHSO$_5$.KHSO$_4$.K$_2$SO$_4$; 0.33 g, 0.55 mmol) in 5 ml of H$_2$O was added dropwise over 5 minutes. The mixture was stirred for 30 minutes as it was allowed to warm to room temperature. The reaction mixture was then diluted with 10 ml of water and extracted 3×10 ml of CHCl$_3$. The organic layers were combined, washed with 15 ml saturated NaCl, dried (MgSO$_4$) and stripped in vacuo to an oil which crystallized on standing. The crystals were triturated with minimal ether to produce 50 mg of present title product; tlc Rf 0.03 (1:1 ethyl acetate:hexane), 0.42 (5:1 ethyl acetate:CH$_3$OH); mp 79°-81° C.; $^1$H-NMR (CDCl$_{3,}$ 250 MHz) delta (ppm) 5.7 (m, 1H), 3.6 (m, 1H), 3.2-2.8 (m+s, 7H), 2.65 (m, 1H).

EXAMPLE 8

3R-(p-Toluenesulfonyloxy) thiolane 1R-Oxide

A solution of 46.30 g (0.179 mol) title product of Example 6 in 600 ml acetone, under nitrogen was cooled to 0° C. In a separate flask 61.73 g (0.100 mol) potassium peroxymonosulfate was stirred in 500 ml distilled water until clear. This was added to the acetone solution at 0° C. and the mixture allowed to warm to room temperature. After 25 minutes 75 ml of 10% (w/v) aqueous sodium sulfite was added, the acetone was evaporated, 300 ml ethyl acetate added and the aqueous layer was extracted with ethyl acetate (3×100 ml). The combined extracts were dried (MgSO$_4$) and concentrated to dryness to yield 48.57 g of crude product. The latter was purified by silica gel chromatography using 10:10:1 ethyl acetate:CH$_2$Cl$_2$:CH$_3$OH as eluant to afford purified title product, 34.67 g (71%); [alpha]$_D$= +4.26° (c=3.0, CHCl$_3$).

EXAMPLE 9

3S-(Acetyl thio) thiolane 1R-Oxide

Method A

In a flame-dried flask under nitrogen, 31.67 g (0.1156 mol) 3R-(p-toluenesulfonyloxy)thiolane 1R-oxide was dissolved in 300 ml acetone and 19.81 g (0.1734 mol) potassium thioacetate was added. The mixture was heated at reflux for 3.5 hours and allowed to stir at room temperature overnight. The mixture was filtered, rinsed and washed with 500 ml acetone and the filtrate and washings were evaporated in vacuo to obtain 23.96 g of the desired product as an oil. The oil was purified by flash chromatography on a 120 mm×25 cm silica gel column eluting with 19:1 ethyl acetate:methanol collecting 125 ml fractions. Fractions 42-64 were combined and stripped to yield purified title product as an oil which crystallized on standing, 16.46 g; (80%); m.p. 51°-52° C.; [alpha]$_D$= -83.41° (c=0 86, . CHCl$_3$).

Analysis calculated for C$_6$H$_{10}$S$_2$O$_2$: C, 40.4; H. 5.6%. Found: C, 40.15; H, 5.53%.

Method B 3R-(Methanesulfonyloxy) thiolane 1R-oxide (90 mg, 0.45 mmol) and potassium thioacetate ( 100 mg, 0.88 mmol) were combined in 5 ml of acetone and refluxed for 3 hours. The reaction mixture was cooled, diluted with 5 ml of ethyl acetate and solids removed by filtration. The mother liquor was stripped of solvents in vacuo and the residual oil chromatographed on silica gel using 1:19 CH$_3$OH:ethyl acetate/0.5% (C$_2$H$_5$)$_3$N as eluant. Product containing fractions were combined and stripped to yield 44 mg of present title product, identical in properties with that produced by Method A.

EXAMPLE 10

Sodium Salt of 3S-(Thio(thiocarbonyl)thio)thiolane 1R-Oxide

In a flame-dried flask under nitrogen, a solution of 1.78 g (10 mmol) 3S-(acetylthio)thiolane 1R-oxide in 6 ml ethanol was cooled to −5° C. Sodium ethoxide (21% by weight in ethanol, 3.73 ml, 10 mmol) was added and the mixture stirred at −5 ° C. for 30 minutes, then cooled to −20° C., 3.0 ml (50 mmol) carbon disulfide added and stirring continued for 30 minutes. To this was added 75 ml anhydrous tetrahydrofuran. The resulting mixture was stirred for a few minutes, seeded with crystals of the title compound, cooled and held at 15° C., and stirred until crystallization was complete. The mixture was filtered, washed with cold tetrahydrofuran and then with ethyl ether. The resulting crystals were air-dried under nitrogen to afford 2.10 g of title product, solvated with 0.5 molar equivalents of tetrahydrofuran. Another 592 mg was recovered by reworking the mother liquor; m.p. 120°–121° C. (dec.), blackens at 155°–156° C.; $[alpha]_D = -79.52°$ (c=0.05, in $H_2O$).

EXAMPLE 11

3R, 4R-3-[1R-1-(Dimethyl-t-butylsilyloxy)ethyl]-4-[1R-oxo-3S-thiolanylthio (thiocarbonyl)thio]-2-azetidinone In a flame-dried flask under $N_2$, a solution of 3R, 4R-4-acetoxy-3-[1R-(dimethyl-t-butylsilyloxy)ethyl]-2-azetidinone [1.87 g, 6.5 mmol; Leanza et al., *Tetrahedron* 39, pp. 2505–2513 (1983)] in 20 ml isopropyl alcohol and $CS_2$ (0.15 ml, 2.5 mmol) were combined and cooled to 3° C. The product of the preceding Example (1.36 g, 5 mmol) was added portionwise, maintaining 3° C. After 0.5 hour at 3° C., the reaction was quenched with 40 ml saturated ammonium chloride solution, and then 50 ml ethyl acetate was added. The organic layer was separated and the aqueous layer was extracted with an additional 2×25 ml ethyl acetate. The combined ethyl acetate layers were washed 2×20 ml $H_2O$ and 2×20 ml 20% $CaCl_2$, dried over $MgSO_4$, filtered and concentrated in vacuo to yield crude title product, 3.04 g. The latter was dissolved in about 2 ml acetone, isopropyl ether was added dropwise until precipitation of solid started, the mixture was stirred for one hour, then 120 ml petroleum ether was added rapidly with stirring. The resulting solid was collected by filtration, air-dried, then dried in vacuo, and finally chromatographed on silica gel using 19:1 ethyl acetate:methanol as eluant to yield 1.35 g (61%) of purified title product. Recrystallization from 4 ml acetone by the same procedure gave back 1.15 g of product; $[alpha]_D = +109.36°$ (c=0.20, $CHCl_3$); pnmr($CDCl_3$) (delta) (ppm) 300 MHz: 0.05 (s, 3H), 0.86 (s, 9H), 1.18 (s, 3H), 1.74 (s, 2H), 2.68 (m, 3H), 2.82 (m, 1H), 3.17 (m, 2H), 3.74 (q, 1H), 4.25 (t, 1H), 4.52 (t, 1H), 5.61 (s, 1H), 6.52 (s, 1H), 7.20 (s, 1H).

EXAMPLE 12

3S,4R-N-[(2-Chloroallyloxy)oxalyl]-3-[1R-(dimethyl-t-butylsilyloxy)ethyl]-4-[1R-oxo-3S-thiolanylthio(thiocarbonyl)thio]-2-azetidinone A flame-dried, three-neck flask equipped with a dropping funnel and low temperature thermometer under a $N_2$ atmosphere was charged with the product of the preceding Example (878 mg, 2 mmol) and 15 ml dry methylene chloride (passed through neutral alumina). The reaction was cooled to −50° to −55° C. internal temperature and N,N-diisopropylethylamine (0.45 ml, 2.6 mmol) was added, keeping the temperature less than −50° C. Then 2-chloroallyl oxalofluoride (0.34 ml, 2.6 mmol) was added as fast as possible, again keeping the temperature below −50° C., and the reaction stirred an additional 50 minutes at −50° to −55° C. The reaction was quenched with 15 ml $H_2O$, allowed to warm to 0° C. and diluted with 20 ml fresh $CH_2Cl_2$. The organic layer was separated, washed 1×15 ml $H_2O$, 1×20 ml pH 7 buffer and 1×25 ml saturated NaCl, dried over $MgSO_4$, filtered and concentrated in vacuo to yield 1.05 g of title product as a yellow foam, all of which was used directly in the next step.

EXAMPLE 13

2-Chloroallyl 5R, 6S-6-[1R-(Dimethyl-t-butylsilyloxy)ethyl]2-(1R-oxo-3S-thiolanylthio)-2-penem-3-carboxylate A flame-dried, three-neck flask equipped with a condenser and an equilibrating addition funnel under a $N_2$ atmosphere was charged with the product of the preceding Example (1.05 g, 2 mmol) and 80 ml ethanol-free chloroform. The reaction was heated to a gentle reflux and triethyl phosphite (0.74 ml, 48 mmol) in 10 ml ethanol-free chloroform was added dropwise over a ten-hour period. The reaction was heated at a gentle reflux for an additional ten hours. The reaction was cooled to room temperature and concentrated in vacuo. The residue was dissolved in 5 ml ethyl acetate. Isopropyl ether (40 ml) was added dropwise with stirring as crystallization began. Finally, 40 ml petroleum ether was added dropwise, the mixture filtered and solids dried to yield 0.47 g (44%) of the product; m.p. 140°–141° C.; $[alpha]_D = +36.78°$ (c=0.5, $CHCl_3$).

EXAMPLE 14

2-Chloroallyl 5R, 6S-6-(1R-Hydroxyethyl)-2-(1R-oxo-3S-thiolakylthio)-2-penem-3-carboxylate A flame-dried, three-neck flask equipped with a thermometer and two addition funnels under a $N_2$ atmosphere was charged with the product of the preceding Example (0.25 g, 0.46 mmol) and 0.5 ml dry tetrahydrofuran. To the stirred reaction was added glacial acetic acid (0.26 ml, 4.6 mmol), followed by tetrabutyl ammonium fluoride in tetrahydrofuran (1M, 1.38 ml). The resulting solution was stirred sixteen hours at room temperature, diluted with 15 ml ethyl acetate and 4 ml water, adjusted to pH 6.4 with potassium acetate, the layers separated, and the organic layer washed 3×3 ml water. The latter were combined and back-washed 3×3 ml $CH_2Cl_2$. The combined organic layers (ethyl acetate and $CH_2Cl_2$) were dried over $Na_2SO_4$, filtered and concentrated in vacuo to yield crude product, 0.46 g. The crude was taken up in 25 ml ethyl acetate and washed 3×6 ml $H_2O$. The organic layer was dried over $Na_2SO_4$, filtered and stripped to yield purified title product, 88 rag; m.p. 177°–178° C.; $[alpha]_D = +45.28°$ (c=0.25 in dimethylsulfoxide).

EXAMPLE 15

Sodium 5R,6R-6-(1R-Hydroxyethyl)-2-(1R-oxo-3S-thiolanyl-thio)-2-penem-3-carboxylate A flame-dried flask wrapped in aluminum foil, under $N_2$, was charged with the product of the preceding Example (3.60 g, 8.5 mmol) in 115 ml of degassed $CH_2Cl_2$, followed by triphenylphosphine (0.72 g, 2.75 mmol), sodium 2-ethylhexanoate (6.72 ml of 1.39M in ethyl acetate, 9.34 mmol) and tetrakis(triphenylphosphine)palladium (0.72 g, 0.62 mmol). The reaction was stirred at room temperature for fifty minutes, an additional 72 mg each of triphenylphosphine and tetrakis(triphenylphosphine)palladium were added and the reaction stirred at room temperature an additional twenty minutes. Hplc purity ethyl acetate (150 ml) was added to the reaction over a fifteen minute period. The reaction was filtered and the solids air-dried to yield crude product, 4.07 g. The latter was slurried with 45 ml ethyl acetate for 45 minutes, filtered and dried to afford 3.96 g of still crude product. The latter was taken up in 70 ml of water, treated with activated carbon, filtered and the filtrate freeze-dried to yield title product, 2.63 g.

EXAMPLE 16

5R, 6S-6-(1R-1-Hydroxyethyl)-2-(1R-oxo-3S-thiolanylthio)-2-penem-3-carboxylic Acid (II, R=H)

The sodium salt of the preceding Example (2.63 g) was dissolved in 8 ml $H_2O$ and cooled to 0°–5° C. The pH was adjusted to 2.45 with 1N HCl as product began to crystallize. The mixture was stirred at 0°–5° C. for forty-five minutes, filtered, washed with a small amount of $H_2O$ and dried to yield 2.16 g of title product as a white solid; mp. 135° C (dec); $[alpha]_D = 366.01°$ (c=1 in dimethylsulfoxide).

EXAMPLE 17

Sterile Sodium 5R,6S-6-(1R-Hydroxyethyl)-2-(1R-oxo-3S-thiolanylthio)-2-penem-3-carboxylate The product of the preceding Example (1.95 g) was suspended in 60 ml $H_2O$ and cooled to 0°–5° C. Maintaining that temperature range and using vigorous stirring, the pH was adjusted from 2.98 to a constant pH of 6.00 by the dropwise addition of NaOH (4.2 ml of 1N, followed by 10.75 ml of 0.1N). The solution was millipore filtered into a sterile flask and freeze-dried (if desired, freeze-dried after subdivision to obtain the desired dosage in rubber-stoppered sterile vials) to yield sterile title product, 1.926 g, which, if not already subdivided, can be subdivided into vials at the desired dosage level. This purified product shows m.p. 158° C. (dec.); $[alpha]_D = +81.31°$ (c=1 in $H_2O$).

For parenteral dosage, the sterile sodium salt is dissolved in sterile water for injection.

EXAMPLE 18

Tetrabutylammonium 5R, 6S-6-[1R-(Dimethyl-t-butylsilyloxy)ethyl]-2-(1R-oxo-3S-thiolanylthio)-2-penem-3-carboxylate The product of Example 13 (0.80 g, 1.5 mmol) was reacted according to Example 15 to form intermediate sodium salt in situ. The reaction mixture was diluted with 35 ml ethyl acetate and 4 ml ether, washed 3×10 ml $H_2O$, the organic layer further diluted with 35 ml hexane, and finally washed 3×20 ml $H_2O$. The six aqueous layers were combined, then further combined with tetrabutylammonium hydrogen sulfate (0.51 g, 1.5 mmol) and $NaHCO_3$ (0.25 g, 3 mmol) in 5 ml $H_2O$. After stirring for 15 minutes and salting with $Na_2SO_4$, the desired product was extracted into $CH_2Cl_2$ (3×90 ml), dried ($Na_2SO_4$), treated with activated carbon, filtered and concentrated in vacuo to yield title product, 0.80 g; pnmr($CDCl_3$)delta(ppm) 300 MHz: 0.05 (s, 6H), 0.85 (s, 9H), 0.99 (t, 12H), 1.28 (d, 3H), 1.30–1.50 (m, 8H), 1.50–1.70 (m, 8H), 2.50–2.82 (m, 4H), 2.96–3.10 (m, 1H), 3.05–3.42 (t, 8H), 3.45–3.62 (m, 2H), 3.80–3.92 (m, 1H), 4.05–4.18 (m, 1H), 5.42 (s, 1H).

EXAMPLE 19

Pivaloyloxymethyl 5R,6S-6-[1R-(Dimethyl-t-butylsilyloxy)ethyl]-2-(1R-oxo-3S-thiolanylthio)-2-penem-3-carboxylate In flame-dried glassware, under $N_2$ the product of the preceding Example (0.80 g, 1.13 mmol) was dissolved in 11 ml acetone. Chloromethyl pivalate (0.25 ml, 1.71 mmol) was added and the mixture stirred 16 hours at room temperature, then stripped in vacuo, finally under high vacuum, to yield title product, 1.05 g; pnmr ($CDCl_3$)delta(ppm) 300 MHz: 0.05 (s, 6H), 0.88 (s, 9H), 1.20 (s, 9H), 1.24 (d, 3H) , 2.4–2.6 (m, 4H), 3.05–3.12 (m, 1H), 3.6–3.90 (m, 3H), 4.15–4.28 (m, 1H), 5.59 (s, 1H), 5.81 (q, 2H, $J_{AB}=12.5$ Hz).

EXAMPLE 20

Pivaloyloxymethyl 5R, 6S-6-(1R-hydroxyethyl-2-(1R-oxo-3S-thiolanylthio)-2-penem-3-carboxylate By the method of Example 9, the product of the preceding Example (0.40 g, 0.69 mmol) was converted to present title product. To isolate, the reaction mixture was diluted with 45 ml ethyl acetate and washed 4×9 ml $H_2O$. The water washes were combined and back extracted 3×9 ml ethyl acetate. All organic layers were combined, washed 2×9 ml saturated NaCl, dried, filtered and concentrated in vacuo, ultimately under high vacuum to yield crude product, 0.28 g. The latter was flash chromatographed on a 40 mm ×25 cm column of silica gel, initially eluting with 1:9 ethyl acetate: tetrahydrofuran (50 ml fractions 1–10), and then with tetrahydrofuran for subsequent 50 ml fractions. Fractions 18–44 were combined, evaporated to dryness, and the residue stirred with 70 ml ethyl acetate and filtered to yield purified title product, 0.193 g; pnmr($CDCl_3$)delta(ppm) 300 MHz: 1.18 (s, 9H), 1.29 (d, 3H, J=6.3 Hz), 2.12 (bs, 1H), 2.6–2.9 (m, 4 Hz), 3.1–3.2 (m, 1H), 3.6–3.90 (m, 3H), 4.20–4.32 (m, 1H), 5.64 (s, 1H), 5.76 (q, 2H, $J_{AB}=12.5$ Hz).

PREPARATION 1

(R)-2-Hydroxy-4-(methylthio) butyric Acid

D-Methionine (100 g, 0.67 mol) was dissolved in 600 ml of 10% $H_2SO_4$ and cooled to 0°–5° C. A solution of $NaNO_2$ (58 g, 0.84 mol) in 100 ml of $H_2O$, also chilled to 0°–5 ° C., was added dropwise over 1.5 hours, maintaining the temperature of the reaction mixture at 10° C. or less by means of an ice water bath. After stirring for 18 hours at room temperature, the mixture was extracted 9×200 ml ethyl acetate. The organic extracts were combined, dried over $MgSO_4$, and stripped to yield 10.1 g of title product as oil; tlc Rf 0.15 (ethyl acetate), 0.08 (1:1 hexane:ethyl acetate).

The same product is alternatively prepared from D-methionine by the diazotization method of Steadman et al., J. Agric. Food Chem., v. 23, pp. 1137-1144 (1975), bioreduction of 2-oxo-4-(methylthio)butyric acid (see footnote [3] of Kleemann et al., Angew. Chem. Int. Ed. Engl., v. 18, p. 797 (1979), or by suitable optical resolution of commercially available racemic 2-hydroxy-4-(methylthio)butyric acid.

PREPARATION 2

(R)-2-Acetoxy-4-(methylthio) butyric Acid

D-Methionine (14.9 g, 0.10 mol) was stirred in 300 ml of acetic acid. Sodium nitrite (13.8 g, 0.2 mol) was added portionwise over 45 minutes while maintaining the temperature in the range 20°-30° C. After stirring for an additional 90 minutes at room temperature, the resulting yellow solution was stripped in vacuo to solids which were distributed between 300 ml each of water and ethyl acetate. The organic layer was separated, washed with saturated NaCl, dried over $MgSO_4$ and stripped to yield 7.0 g of title product as a yellow oil, used directly in the next step; tlc Rf 0.08 (3:1 hexane:ethyl acetate).

PREPARATION 3

Methyl (R)-2-Hydroxy-4-(methylthio) butyrate

Method A

The entire product of the preceding Preparation (7.0 g) was taken up in 100 ml of $CH_3OH$ and 0.7 ml of $H_2SO_4$ added. The mixture was heated at reflux for 3 hours, stripped of methanol in vacuo, and the residue dissolved in 250 ml ethyl acetate. The resulting solution was washed in sequence with 150 ml each of $H_2O$, saturated $NaHCO_3$ and brine, and restripped to an oil, which was chromatographed on 100 g of silica gel using 5:1 hexane:ethyl acetate to elute a less polar impurity and 3:1 hexane:ethyl acetate to elute 2.8 g of present title product; tlc Rf 0.33 (3:1 hexane:ethyl acetate) 0.50 (1:1 hexane:ethyl acetate), 0.90 (ethyl acetate: [alpha]$_D$=+15.6 (c=1, $CH_3OH$); $^1$H-NMR ($CDCl_3$, 300 MHz) delta (ppm) 4.3 (m, 1H), 3.74 (s, 3H, $OCH_3$), 2.8 (bs, 1H, OH), 2.6 (m, 2H), 2.1 (s+m, 4H), 1.9 (m, 1H).

Method B

Title product of Preparation 1 (10.1 g, 0.067 mol), 15 ml of $CH_3OH$, 0.5 ml of $H_2SO_4$ and 200 ml of $CHCl_3$ were combined and warmed at 40° C. for 3 hours. The mixture was washed in sequence with 125 ml each of $H_2O$, saturated $NaHCO_3$ and brine, dried over $MgSO_4$ and stripped to yield 7.5 of title product as an oil, having properties as in Method A.

PREPARATION 4

(R)-4-(Methylthio)-1,2-butanediol

Title product of the preceding Preparation (3.0 g, 0.018 mol) was dissolved in 25 ml of tetrahydrofuran. Water (2.5 ml) was added and the mixture cooled to 0°-5° C. $NaBH_4$ (0.7 g, 0.018 tool, 0.072 equivalents) was then added and the mixture stirred for 18 hours as its temperature slowly increased to room temperature. The reaction mixture was quenched by slowly adding 1.5 ml 12N HCl with vigorous stirring. The quenched mixture was diluted with an equal volume of ethyl acetate, dried over $MgSO_4$, stripped, and the resulting residue chromatographed on silica gel using ethyl acetate as eluant to yield 2.2 g of present title product; tlc Rf 0.8 (ethyl acetate); [alpha]$_D$=+39.1° (c=1.2, $CH_3OH$); literature, [alpha]$_D^{25}$=+37° (c=2.5, $CH_3OH$), Steadman et al., loc. cit.

This preparation was repeated using 7.5 g (0.046 mol) of title product of the preceding Preparation to yield 6.4 g of crude title product and, following chromatography on 120 g of silica gel using gradient elution with 300 ml each of $CHCl_3$, 1:1 $CHCl_3$:ethyl acetate, 1:2 $CHCl_3$:ethyl acetate and ethyl acetate, 4.4 g of purified title product, having identical tlc properties and [alpha]$_D$=−39.9° (c=1.62, methanol).

The same product is alternatively obtained by $LiAlH_4$ reduction of ethyl (R)-2-hydroxy-4-(methylthio)butyrate according to the method used by Steadman et al., loc. cit., for the preparation of the corresponding (S)-enantiomer, or by suitable optical resolution of the racemic title product of Preparation 6, e.g., by the method of Steadman et al., loc. cit., who obtained present title product via resolution of the phthalate half ester with L-amphetamine.

PREPARATION 5

Racemic Methyl 2-Hydroxy-4-(methylthio) butyrate

Commercial calcium 2-hydroxy-4-(methylthio)butyrate (20 g, 0.12 mol) was suspended in 250 ml $CH_2Cl_2$. $CH_3OH$ (15 ml, 0.36 mol) was added and the mixture cooled to 10° C., at which point $H_2SO_4$ (3.7 ml, 0.07 mol) was added. An obvious physical change in the slurry was noted. The mixture was heated at reflux for 60 minutes, by which time tlc indicated reaction was nearly complete. As a matter of convenience, the reaction mixture was stirred 64 hours at room temperature, at which time insoluble byproducts were removed by filtration. The filtrate was washed with 150 ml each of saturated $NaHCO_3$ and brine, dried ($MgSO_4$) and stripped to yield title product as an oil; tlc Rf 0.8 (ethyl acetate)0.25 (3:1 hexane:ethyl acetate).

PREPARATION 6

Racemic 4-(Methylthio)-1,2-butanediol

Title product of the preceding Preparation (15.0 g, 0.09 mol) was dissolved in a mixture of 100 ml of tetrahydrofuran and 10 ml of $H_2O$. $NaBH_4$ (4.9 g, 0.13 mol, 0.52 equivalents) was added portionwise over 15 minutes, during which time the temperature rose to 30° C. After stirring for 3 hours at room temperature, the reaction mixture was diluted with 200 ml of ice water and 200 ml of ethyl acetate. Following thorough mixing, the organic layer was separated, washed with 125 ml saturated NaCl. The combined aqueous layer and NaCl extract were saturated with NaCl and extracted with 250 ml of ethyl acetate. The two organic layers were combined, dried ($MgSO_4$) and stripped to yield 8.3 g of present title product; tlc Rf 0.45 (ethyl acetate).

Present title product is alternatively prepared from 3-butene-1,2-diol according to the method of Steadman et al., loc. cit.

PREPARATION 7

(2-Chloroallyl)oxalyl Chloride [2-Chlorlallyl Oxalochloride]

A 1-liter 3-necked flask was equipped with a stirrer, thermometer, cooling bath, and nitrogen purge. Methylene chloride (160 ml) and oxalyl chloride (106 ml, 154 g, 1.21 moles) were charged and the solution was cooled to 0° C. Chloroallyl alcohol (107 g, 1.17 moles) was added dropwise. The solution was stirred and allowed to warm to room temperature. The solution was concentrated at reduced pressure and the product distilled at 50° C. and 3-2 mm Hg giving 81.7% yield of the desired product; $^1$H-NMR 60 MHz (neat) delta (ppm) 5.7 (m, 1H), 5.5 (m, 1H), 5.0 (s, 2H).

PREPARATION 8

(2-Chloroallyl)oxalyl Fluoride [2-Chloroallyl Oxalofluoride]

A 22-liter 3-necked flask was equipped with mechanical stirrer, thermometer, addition funnel, condenser, and nitrogen purge. The flask was charged with 16 l of acetonitrile and 785 g (13.5 moles) of potassium fluoride. The slurry was heated to reflux, and (2-chloroallyl)oxalyl chloride (2.0 Kg, 10.9 mol) was added dropwise with stirring over 22 minutes. The addition helps keep the reaction at reflux. The reaction was heated another 30 minutes, then cooled to 25° C. The salts were removed by filtration and the product was concentrated at reduced pressure. The product was distilled at 0.2 to 1 mm Hg and. 51°-53° C. giving 1.4 Kg (78% yield) of an off-white, clear liquid; $^1$H-NMR 60 MHz (neat) delta (ppm) 5.8 (m, 1H), 5.6 (m, 1H), 5.0 ( s, 2H).

I claim:

1. A process for the preparation of an optically active compound of the formula

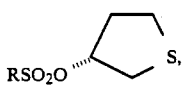

(I)

wherein R is (C$_1$-C$_3$) alkyl, phenyl or tolyl, which comprises the steps of:

(a) reacting an optically active diol of the formula

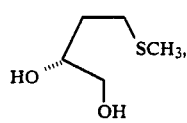

(II)

in a reaction-inert solvent with at least 2 molar equivalents of RSO$_2$Cl in the presence of at least 2 equivalents of a tertiary amine to form an optically active disulfonate of the formula

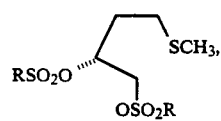

(III)

(b) with or without isolation, allowing to stand or heating the disulfonate of the formula (III) neat or in the same or another reaction-insert solvent to form an optically active sulfonium salt of the formula

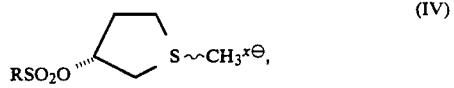

(IV)

wherein X is RSO$_3$ or halogen; and (c) with or without isolation, heating the sulfonium salt of the formula (IV) with up to three molar equivalents of an additional nucleophilic anion in the same or another reaction-inert solvent to form the compound of the formula (I).

2. A process of claim 1 wherein R is CH$_3$.

3. A process of claim 1 wherein R is p-tolyl.

4. A process of claim 1 wherein substantially two equivalents of the acid chloride are employed in an excess of pyridine as tertiary amine and as reaction-inert solvent, without isolation of the intermediate compounds of the formulas (III) and (IV).

5. A process of claim 4 wherein R is CH$_3$.

6. A process of claim 4 wherein R is p-tolyl.

7. A process of claim 1 which further comprises the preparation of the diol of the formula (II) by the steps of (d) diazotization of D-methionine with NaNO$_2$ in acetic acid to form an optically active acetoxy acid of the formula

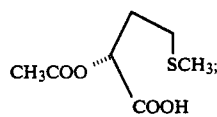

(V)

(e) concurrent solvolysis and esterification of the acetoxy acid of the formula (V) by reaction with excess methanol in the presence of a catalytic amount of a strong acid to form an optically active hydroxy ester of the formula

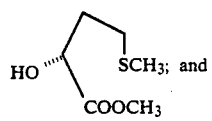

(VI)

(f) hydride reduction of the hydroxy ester of the formula (VI) to form the diol of the formula (II).

8. A process of claim 1 which further comprises oxidation of the compound of the formula (I) to form an optically active sulfoxide of the formula

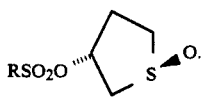

(VII)

9. A process of claim 8 wherein R is CH$_3$.

* * * * *